US012565541B1

(12) United States Patent
Eid et al.

(10) Patent No.: US 12,565,541 B1
(45) Date of Patent: Mar. 3, 2026

(54) METHOD FOR EXTRACTING UNFRACTIONATED HEPARIN FROM CAMEL INTESTINAL MUCOSA

(71) Applicant: Camelx Biomedical & Research, Riyadh (SA)

(72) Inventors: Eltayeb E.M. Eid, Riyadh (SA); Huaijun Yun, Kaizhou (CN); Mohamed Diriye, Riyadh (SA); Alshaima Hamidaddin, Riyadh (SA)

(73) Assignee: Camelx Biomedical & Research, Riyadh (SA)

( * ) Notice: Subject to any disclaimer, the term of this patent is extended or adjusted under 35 U.S.C. 154(b) by 0 days.

(21) Appl. No.: 19/317,897

(22) Filed: Sep. 3, 2025

(51) Int. Cl.
*C08B 37/00* (2006.01)
*C12N 9/74* (2006.01)

(52) U.S. Cl.
CPC ...... *C08B 37/0075* (2013.01); *C08B 37/0003* (2013.01); *C12N 9/6429* (2013.01); *C12Y 304/21004* (2013.01)

(58) Field of Classification Search
CPC ............ C08B 37/0075; C08B 37/0003; C12N 9/6429; C12Y 304/21004
See application file for complete search history.

(56) References Cited

U.S. PATENT DOCUMENTS

| | | | |
|---|---|---|---|
| 6,232,093 | B1 | 5/2001 | Van Houdenhoven et al. |
| 9,770,419 | B2 | 9/2017 | Mousa et al. |
| 2025/0101140 | A1 | 3/2025 | Escaich Ferrer et al. |

FOREIGN PATENT DOCUMENTS

| | | | | |
|---|---|---|---|---|
| CN | 103755838 | A | * | 4/2014 |
| CN | 104479047 | A | * | 4/2015 |
| CN | 105175578 | A | * | 12/2015 |
| CN | 118460646 | A | * | 8/2024 | ......... C08B 37/0075 |
| EP | 3821025 | A1 | | 7/2019 |
| WO | 2010110654 | A1 | | 3/2009 |

OTHER PUBLICATIONS

English language machine translation of CN105175578A; translated Nov. 7, 2025. (Year: 2015).*
English language machine translation of CN118460646A; translated Nov. 7, 2025. (Year: 2024).*
English language machine translation of CN103755838A; translated Nov. 11, 2025. (Year: 2014).*
English language machine translation of CN104479047A; translated Nov. 11, 2025. (Year: 2015).*
Wang, H.; et al. "Determination of the pKa of glucuronic acid and the carboxy groups of heparin by 13C-nuclear-magnetic-resonance spectroscopy", Biochemical Journal 1991, vol. 278, pp. 689-695. (Year: 1991).*
Weiss, R. J.; et al. "Targeting heparin and heparan sulfate protein interactions", Organic Biomolecular Chemistry 2017, vol. 15, pp. 5656-5668. (Year: 2017).*
Strazzullo, P.; et al. "Sodium", Advances in Nutrition 2014, vol. 5, pp. 188-190. (Year: 2014).*
Mohamad Warda et al.; "Isolation and characterization of raw heparin from dromedary", DOI: https://doi.org/10.1016/j.cca.2003.10.009, Dec. 2003.
Omozusi Andrews, et al.; "Processing bovine intestinal mucosa to active heparin removes spiked BSE", DOI: https://doi.org/10.1016/j.biologicals.2020.06.004, Sep. 2020.
Ahmad Almeman, et al.; "Detection and Extraction of Heparin from Camel Lungs", DOI: 10.2174/1389201020666190401145544, 2019.

* cited by examiner

*Primary Examiner* — Andrea Olson
*Assistant Examiner* — Benjamin M Brandsen
(74) *Attorney, Agent, or Firm* — Nath, Goldberg & Meyer; Joshua B. Goldberg

(57) ABSTRACT

The present subject matter relates to an extraction procedure of unfractionated heparin from camel intestinal mucosa. The method includes a successful pretreatment procedure to obtain a maximum amount and good quality of mucosa from mast cells in camel intestines. The present disclosures addresses the issues with other heparin sources by providing a very potent unfractionated heparin derived from the intestinal mucosa of camels that are well-adapted desert animals with unique body biochemistry and physiology.

17 Claims, 9 Drawing Sheets

1

METHOD FOR EXTRACTING UNFRACTIONATED HEPARIN FROM CAMEL INTESTINAL MUCOSA

BACKGROUND

1. Field

The disclosure of the present patent application relates to an extraction method and, particularly, to a method of extracting unfractionated heparin from camel intestinal mucosa.

2. Description of the Related Art

Currently, 99% of the unfractionated heparin (UFH) consumed worldwide is sourced from porcine intestine mucosa, with ~80% of the production concentrated in China. Such a single animal source from a single country has been shown to be insufficient to meet the growing worldwide demand and is susceptible to sudden shortages caused by porcine epidemics. On the other hand, bovine derived heparin accounts for only 1% of the UFH consumed worldwide, and bovine sources of heparin are in the development process and not yet established. Therefore, more efforts for exploring other heparin sources are necessary to avoid a potential shortage of heparin. Thus, a new source and method of extracting heparin is desired.

SUMMARY

The present subject matter relates to an extraction procedure of unfractionated heparin from camel intestinal mucosa. The method includes a successful pretreatment procedure to obtain a maximum amount and good quality of mucosa from mast cells in camel intestines. The present disclosures addresses the issues described above by providing a potent unfractionated heparin derived from the intestinal mucosa of camels that are well-adapted desert animals with unique body biochemistry and physiology.

A method of removing mucosa from a camel includes removing a small intestine of the camel after slaughtering the camel; washing the small intestine with water; massaging the small intestine; soaking the small intestine in a water bath; pressing the small intestine from a first side of a length of the small intestine to a second side of the length of the small intestine; wherein pressing the small intestine releases at least about 60% of pure mucosa from the small intestine; leaving the small intestine to rest for at least about 10 minutes; and pressing the small intestine for a second time to release 40% of the remaining amount of the pure mucosa.

In certain embodiments, the present methods may include obtaining heparin from the camel mucosa. The method may further include adding calcium chloride to the mucosa to obtain a first mixture, wherein the calcium chloride calcifies the mucosa; removing excessive calcium chloride from the mixture by adding sodium carbonate to create a second mixture; adding hydrogen peroxide to the second mixture to obtain pure mucosa; transferring the pure mucosa to a stainless-steel container; raising the temperature of the pure mucosa; adding sodium chloride to the pure mucosa to create a third mixture, the sodium chloride being about 5% to about 15% w/v and iodine free; adjusting the pH of the third mixture to a value ranging from at least about 8 to at least about 10; raising the temperature of the pure mucosa to at least about 40° C. to at least about 60° C.; adding protease to the pure mucosa to obtain a fourth mixture, and leaving the fourth mixture to react for at least about 2 hours to at least about 5 hours; adding calcium chloride to the fourth mixture to create a fifth mixture, wherein the calcium chloride is a 2-8% solution; raising the temperature of the fifth mixture to at least about 80° C. to at least about 100° C. and leaving the third mixture to react for a period of time ranging from at least about 0.5 hours to at least about 2 hours; adding sodium carbonate to the fifth mixture to obtain a solution and allowing the solution to react for at least about 0.5 hours to at least about 2 hours, wherein the sodium carbonate is a 2-5% w/v solution; allowing the solution to cool; centrifuging the cooled solution and collecting a first clear solution; adjusting the pH of the first clear solution, wherein the pH of the first clear solution is adjusted to a value ranging from at least about 9 to at least about 12; resting the first clear solution for a period of time ranging from at least about 0.5 hours to at least about 2 hours; centrifuging the first clear solution and collecting a second clear solution; adjusting the temperature of the second clear solution to at least about –10° C.; adjusting the pH of the second clear solution to a temperature ranging from about 1 to about 4 and resting the second clear solution for at least about 0.5 hours to at least about 2 hours; centrifuging the second clear solution and collecting a third clear solution; adjusting the pH of the third clear solution to a value ranging from at least about 9 to at least about 12; adding 1-4% w/v $H_2O_2$ to the third clear solution to form a sixth mixture and maintaining the temperature of the sixth mixture at a temperature of at least about 20° C. to at least about 30° C. for at least about 30 hours to at least about 50 hours; centrifuging the sixth mixture and collecting a fourth clear solution; adjusting the pH of the fourth clear solution to at least about 9 to at least about 12, wherein the pH of the fourth clear solution is adjusted by adding 1-3% w/v $H_2O_2$; maintaining a temperature of the fourth clear solution at about 30° C. to about 50° C. for at least about 10 hours to at least about 20 hours; collecting a fifth clear solution through centrifugation and filtration; adding a 10-20% w/v iodine free sodium chloride to the fifth clear solution to obtain a seventh mixture; keeping the seventh mixture overnight; diluting the seventh mixture with water 5 to 10 times to obtain a sixth mixture; adding 0.5 volume of pure ethanol into the seventh mixture; adjusting a temperature of the seventh mixture to about –30° C.; keeping the seventh mixture overnight; and collecting and drying a pure precipitate to obtain a pure unfractionated heparin.

These and other features of the present subject matter will become readily apparent upon further review of the following specification.

DETAILED DESCRIPTION OF THE PREFERRED EMBODIMENTS

Figure 1:
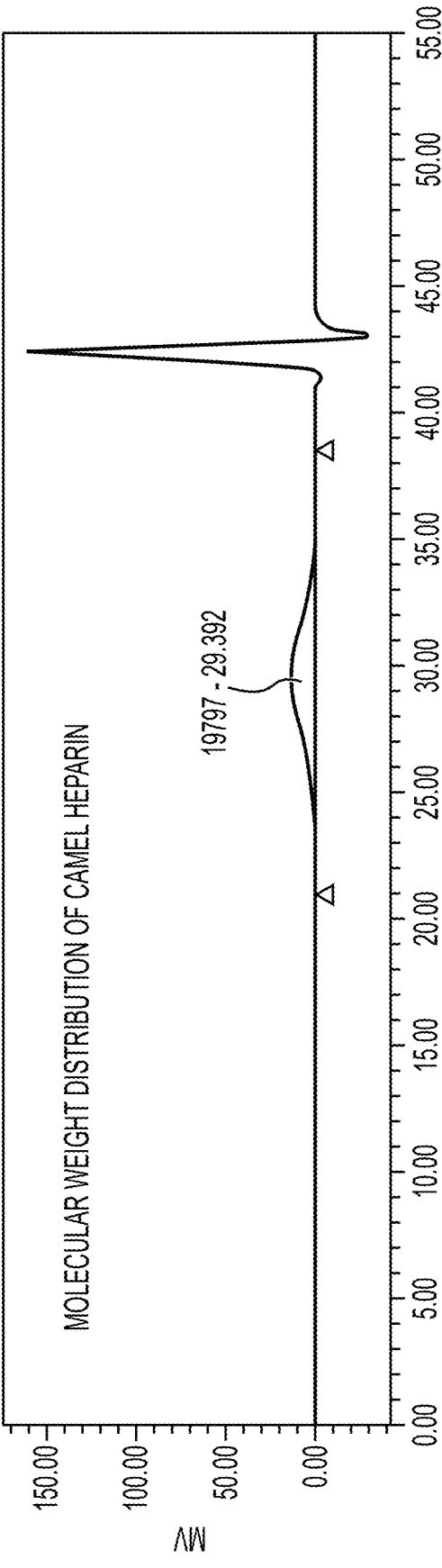
FIG. 1 shows a mass spectrograph of the molecular weight of Camel Heparin.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as disorders of the blood, including clots and other ailments. The present disclosure relates to an extraction procedure of unfractionated heparin from camel intestinal mucosa, exploring the feasibility of a new source of unfractionated heparin derived from dromedary camel. The method may provide a successful pretreatment procedure to obtain a maximum amount of mucosal cells from mast cells in camel intestines. Heparin may be separated from the mucosa and purified to remove organic and inorganic impurities to produce a pharmaceutical grade of heparin sodium which can be applicable to treat and possibly cure blood diseases such as, by non-limiting example, deep-vein thrombosis in patients.

The method may include inactivating viruses in the mucosa from the camel to prevent any potential risk of camel disease transmissible to human beings. The process described herein produced a pure unfractionated heparin derived from camel intestinal mucosa with a molecular weight of 23,567 Daltons, compared to 14100, 14500 and 15921 Daltons for bovine, ovine, and porcine, respectively. The extracted heparin described herein has a lower activated partial thromboplastin time (aPTT) activity of 67.9 IU/mg compared to 160, 190 and 208 IU/mg for bovine, ovine, and porcine respectively.

In an embodiment of a method of removing mucosa from a camel, the method includes removing a small intestine of the camel after slaughtering of the camel. In various embodiments, the camel may be slaughtered according to normal procedures. The method may also include washing the small intestine with water. In the various embodiments, washing the small intestine may remove food residues and impurities inside a wall of the intestine. The method may also include massaging the small intestine. In some embodiments, the small intestine is massaged for at least about 15 minutes, at least 15 minutes, and about 15 minutes. In additional embodiments, a whole portion of the intestine may be massaged. The method further includes soaking the small intestine in a water bath. In some embodiments, the water bath may be at a temperature of at least about 37.0° C., at least 37° C., and about 37° C. In still other embodiments, the soaking may last for at least about 30 minutes, at least 30 minutes, or about 30 minutes to at least about 50 minutes, at least 50 minutes, and about 50 minutes.

The small intestine may be pressed from a first side of a length of the small intestine to a second side of the length of the small intestine. In various embodiments, pressing the small intestine may last for at least about 35 minutes, at least 35 minutes, or about 35 minutes to at least about 40 minutes, at least 40 minutes, or about 40 minutes. In some embodiments, pressing the small intestine releases at least about 60%, at least 60%, or about 60% of the pure mucosa from the small intestine.

The method may also include leaving the small intestine to rest for at least about 10 minutes, at least 10 minutes, or about 10 minutes. The method then includes pressing the small intestine for a second time to release a remaining amount of the pure mucosa. In some embodiments, the remaining amount of the pure mucosa is at least about 40%, at least 40%, or about 40%.

In an embodiment, heparin sodium can be obtained from the mucosa extracted from the camel. The method includes adding calcium chloride to the mucosa to obtain a first mixture. In embodiments, the calcium chloride calcifies the mucosa. In various embodiments, the calcium chloride may be a 2-8% w/v solution. The method may include removing excessive calcium chloride from the first mixture by adding sodium carbonate to create a second mixture. In various embodiments, the method further includes filtering sodium chloride from the second mixture. In other embodiments, filtering the sodium chloride may remove impurities such as, by non-limiting example, proteinic impurities and nucleic impurities. In further embodiments, the sodium chloride may be filtered out by adjusting the pH of the second mixture.

The method may include adding a 1-4% w/v solution of $H_2O_2$ to the second mixture to obtain pure mucosa. The method then includes transferring the pure mucosa to a stainless-steel container and raising the temperature of the pure mucosa. In various embodiments, the temperature may be raised using steam and/or hot water. In other embodiments, the temperature may be raised using a water bath. By way of non-limiting example, the temperature of the mucosa may be raised to at least about 37° C., at least 37° C., or about 37° C. Then, the method may include adding sodium chloride to the pure mucosa to create a third mixture. In various embodiments, the sodium chloride is 5-15% w/v and iodine free.

The method may then include adjusting the pH of the third mixture to a value ranging from at least about 8 to at least about 10. In various embodiments, the pH may be adjusted to at least about 1 to at least about 4. In some embodiments, the pH is lowered using hydrochloric acid. In various embodiments, the pH may be raised by adding sodium hydroxide. Said another way, for a pH in the alkaline range, sodium hydroxide can be used to adjust the pH. The method may then include raising the temperature of the pure mucosa to at least about 40° C., at least 40° C., or about 40° C. to at least about 60° C., at least 60° C., or about 60° C.

The method may include adding protease to the third mixture to obtain a fourth mixture and leaving the fourth mixture to react for at least about 2 hours, at least 2 hours, or about 2 hours to at least about 5 hours, at least 5 hours, or about 5 hours. The method then includes adding calcium chloride to the fourth mixture to create a fifth mixture. In various embodiments, the calcium chloride may be a 2-8% w/v solution. The method then includes raising the temperature of the fifth mixture to at least about 80° C., at least 80° C., or about 80° C., to at least about 100° C., at least 100° C., or about 100° C. The third mixture may then be left to react for at least about 0.5 hours, at least 0.5 hours, or about 0.5 hours, to at least about 2 hours, at least 2 hours, or about 2 hours.

The method may then include adding sodium carbonate to the fifth mixture to obtain a solution and allowing the solution to react for at least about 0.5 hours, at least 0.5 hours, or 0.5 hours, to at least about 2 hours, about 2 hours, or at least 2 hours. In various embodiments, the sodium carbonate may be a 2-5% w/v solution. The solution may then be allowed to cool. In various embodiments, the temperature may be cooled from an initial temperature of at least about 80° C. to at least 100° C. to a temperature below 10° C. The method may then include centrifuging the cooled solution and collecting a first clear solution. The method may then include adjusting the pH of the first clear solution. In other embodiments, the pH of the first clear solution may be adjusted to at least about 9 to at least about 12. The method may then include resting the first clear solution for at least about 0.5 hours, at least 0.5 hours, or about 0.5 hours, to at least about 2 hours, about 2 hours, or at least 2 hours.

The method may then include centrifuging the first clear solution and collecting a second clear solution therefrom. The method may then include adjusting the temperature of the second clear solution to at least about −10° C., at least −10° C., or about −10° C. The method may then include adjusting the pH of the second clear solution to a value ranging from about 1 to about 4 and resting the second clear solution for at least about 0.5 hours, at least 0.5 hours, or about 0.5 hours to at least about 2 hours, at least 2 hours, or about 2 hours. The method may then include centrifuging the second clear solution and collecting a third clear solution and adjusting the pH of the third clear solution to a value ranging from at least about 9 to at least about 12. The method may then include adding 1-4% w/v $H_2O_2$ to the third clear solution to form a sixth mixture and maintaining the temperature of the sixth mixture at a temperature of at least about 20° C., at least 20° C., or about 20° C. to at least about 30° C., at least 30° C., or about 30° C. for at least about 30 hours, at least 30 hours, or about 30 hours to at least about 50 hours, at least 50 hours, or about 50 hours.

The method may then include centrifuging the sixth mixture and collecting a fourth clear solution. In various embodiments, the fourth clear solution may be collected through filtration. The method may then include adjusting a pH of the fourth clear solution to a value ranging from at least about 9 to at least about 12. In further embodiments, the pH of the fourth clear solution is adjusted by adding 1-3% w/v $H_2O_2$. The method may then include maintaining the temperature of the fourth clear solution at a temperature of at least about 30° C., at least 30° C., or about 30° C. to at least about 50° C., at least 50° C., or about 50° C., for at least about 10 hours, at least 10 hours, or about 10 hours to at least about 20 hours, about 20 hours, or at least 20 hours.

The method may then include collecting a fifth clear solution through centrifugation and filtration. The method may include adding a 10-20% w/v iodine free sodium chloride to the fifth clear solution to obtain a sixth mixture and keeping the sixth mixture overnight. In various embodiments, the sixth mixture may be kept for at least about 10 hours, at least 10 hours, or about 10 hours. The method may then include diluting the sixth mixture with water 5 to 10 times to obtain a seventh mixture. In various embodiments, the seventh mixture may be nano-filtered to 5-10% of the original volume of the sixth mixture. By non-limiting example, nanofiltration can be used to selectively remove substances, resulting in a diluted solution in some cases. While in other cases, its primary application is in separation and purification processes.

The method may then include, by way of non-limiting example, adding 0.5 volume of pure ethanol to form a seventh mixture and adjusting the temperature of the seventh mixture to at least about −30° C., at least −30° C., or about −30° C. In this regard, if 100 mL of pure extract is produced, 50 mL, or a 0.5 volume, of ethanol is added to the pure extract. The method may then include keeping the seventh mixture overnight. As previously described overnight may include at least about 8 hours, at least 8 hours, or about 8 hours to at least about 10 hours, at least 10 hours, or about 10 hours. The method may then include collecting and drying a pure precipitate to obtain a pure unfractionated heparin (UFH).

In various embodiments, the pure unfractionated heparin may have a molecular weight of about 24,000 Daltons (DA). Current existing sources of heparin, such Bovine, Ovine and Porcine have been found to have extracted molecular weights of 14100, 14500 and 15921 Da respectively. The higher molecular weight may reduce the risk of bleeding and may be very potent as an anticoagulant.

In some embodiments, the pure UFH may have a potency of 69.8 IU/mg.

In other embodiments, the pure UFH may have an activated partial thromboplastin (aPPT) of about 69.8 IU/mg.

In still other embodiments, a precipitated heparin sodium is produced from the pure UFH.

In another embodiment, the precipitated heparin sodium has an anti-factor IIa concentration of around 120 IU/mg.

EXAMPLES

The small intestine of a camel was removed immediately after slaughtering. It was then washed with water to remove food residues and any impurities inside the wall of the intestine. A gentle massage was applied for 15 minutes to the whole intestine, and then it was soaked in a water bath at 37.0±1° C. for 30-50 minutes. The intestine was pressed firmly from one side to the other side throughout the length of the small intestine (35-40 minutes) to release 60% the pure mucosa. Then the intestine was relaxed for 10 minutes and again was pressed to release the remaining 40% of pure mucosa.

The released mucosa was then calcified using 2-8% calcium chloride at 80-100° C. for 0.5-2 hours. Then, sodium carbonate was applied to remove excessive calcium chloride from the mixture which was ultimately filtered to remove proteinic impurity and nucleic impurity by pH adjustment. Finally, it was treated with 1-4% $H_2O_2$.

The pure mucosa was transferred to a clean stainless-steel container and the temperature was raised to 30-40 C°. A 5-15% w/w iodine free sodium chloride was added to the mucosa and the pH was adjusted to 8-10. Then the temperature was raised to 40-60° C. Next, a 0.1-1% w/v protease was added to the mixture and left to react for 2-5 hours. Calcium chloride (2-8% w/v) was added and then the temperature was raised to 80-100° C. The reaction was left for 0.5-2 hours, then a 2-5% w/v sodium carbonate solution was added to the reaction vessel. The reaction was then left for 0.5-2 hours. Next, the solution was cooled and centrifuged and a clear solution was collected.

A pH of the clear solution was adjusted to a value ranging from 9 to 12 and kept for 0.5-2 hours. The mixture was then centrifuged, and a clear solution was collected. The temperature was adjusted below 10° C. and the pH was adjusted to 1-4 then kept for 0.5-2 hours. Then, the solution was centrifuged, and the clear solution was collected.

The pH of the collected clear solution was adjusted to a value ranging from 9 to 12, then 1-4% w/v $H_2O_2$ was added, and the temperature was kept at 20-30 C° for 30-50 hours. After centrifuge and filtration, a clear solution was collected, then the pH was adjusted to a value ranging from 9 to 12. A 1-3% w/v $H_2O_2$ was added into the solution. Then, the temperature was maintained at 30-50° C. for 10-20 hours. A clear solution was collected after centrifugation and filtration.

A 10-20% w/v iodine-free sodium chloride solution was added to the clear solution and the mixture was kept overnight. The mixture was then diluted with water 5-10 times. Nano filters were used to dilute the solution to 5-10% of the original volume. Nanofiltration can be used to selectively remove substances, resulting in a diluted solution in some cases. Nanofiltration is primarily used for separation and purification processes, not as a general-purpose dilution method. Then, 0.5 volume of pure ethanol was added into the solution and the temperature was adjusted to below 30 C° (−30° C.). In other words, if 100 mL pure extract was produced, 50 mL ethanol is added to the pure extract, i.e. 0.5 volume.

Then, the solution was kept overnight. A pure precipitate was then collected, dried, and a pure unfractionated heparin (UFH) was collected for further investigations.

Results

Figure 2:
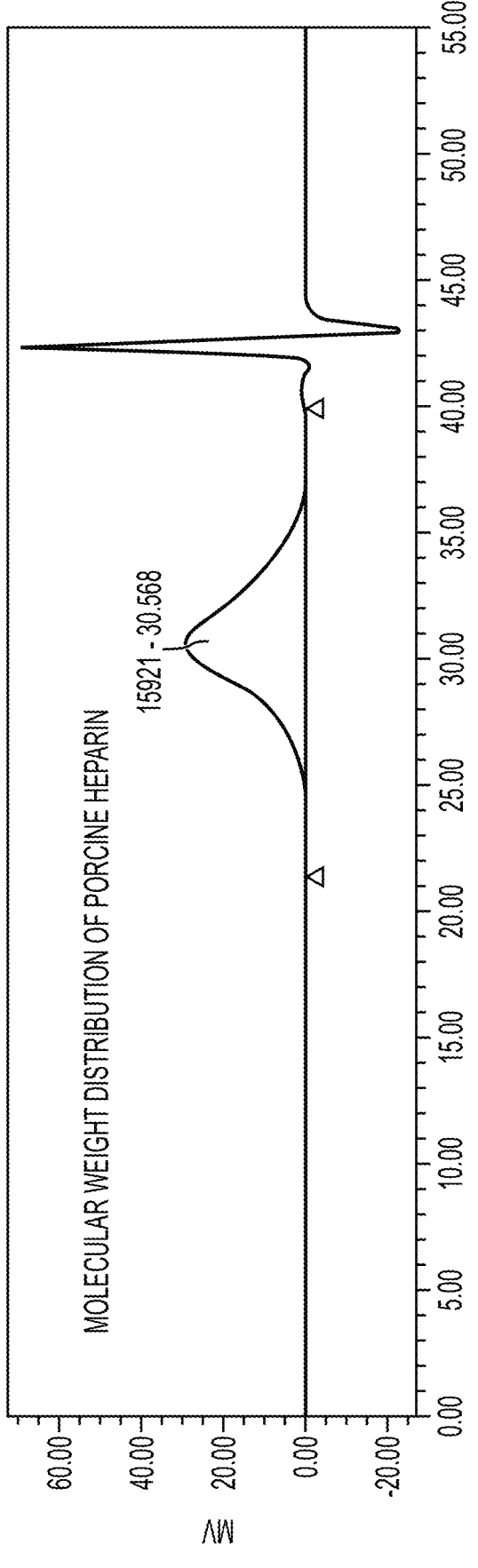
FIG. 2 shows a mass spectrograph of the molecular weight of Porcine Heparin.

The molecular weight of the extracted unfractionated heparin (UFH) from the camel was found to be ~24000 Da, as illustrated in FIG. 1. Current existing sources of heparin, such Bovine, Ovine and Porcine, as illustrated in FIG. 2, have an extracted molecular weight of 14100, 14500 and 15921 Da, respectively. The higher molecular weight can reduce the risk of bleeding and be very potent as well as an anticoagulant.

The tested potency of the UFH extracted from the camel through the activated partial thromboplastin time (aPTT) was found to be 69.8 IU/mg that was considered to be three times better than the existing sources of UFH. The data is presented in Table 1 below.

TABLE 1

| | | | | | |
|---|---|---|---|---|---|
| the in vitro testing of the unfractionated camel heparin compared to other animal sources | | | | | |
| Heparin Source | Molecular Weight (Da) | Potency (i.u./mg) anti-IIa | anti-Xa | aPTT | Ratio aIIa/ aXa |
| Camel | 23567 | 118.7 | 120.5 | 69.8 | 0.9851 |
| Bovine | 14100 | 110 | 108 | 160 | 0.9818 |
| Ovine | 14500 | 188 | 191 | 190 | 1.0160 |
| Porcine | 15921 | 195 | 205 | 208 | 1.0513 |

The camel UFH heparin shows a lower aPTT value with an increased safety in bleeding risk that is three times better than the existing UFH. Higher aPTT values are associated with significant bleeding, and it is well reported that for every 10-second increase in aPTT, the probability of major bleeding will be increased by 7%. A large contemporary scientific report has concluded that bleeding risk was positively correlated with aPTT. Therefore, our findings of aPTT from the camel intestinal mucosa were found to be 69.8 IU/mg compared to the existing one from the porcine source that was 208 IU/mg. Here, the conclusion is that the camel heparin source was found to be higher in bleeding safety compared to others.

The characterized UFH may be a precursor for the production of low molecular heparin after depolymerization of UFH, yielding a product with improved pharmacokinetic characteristics.

Figure 3:
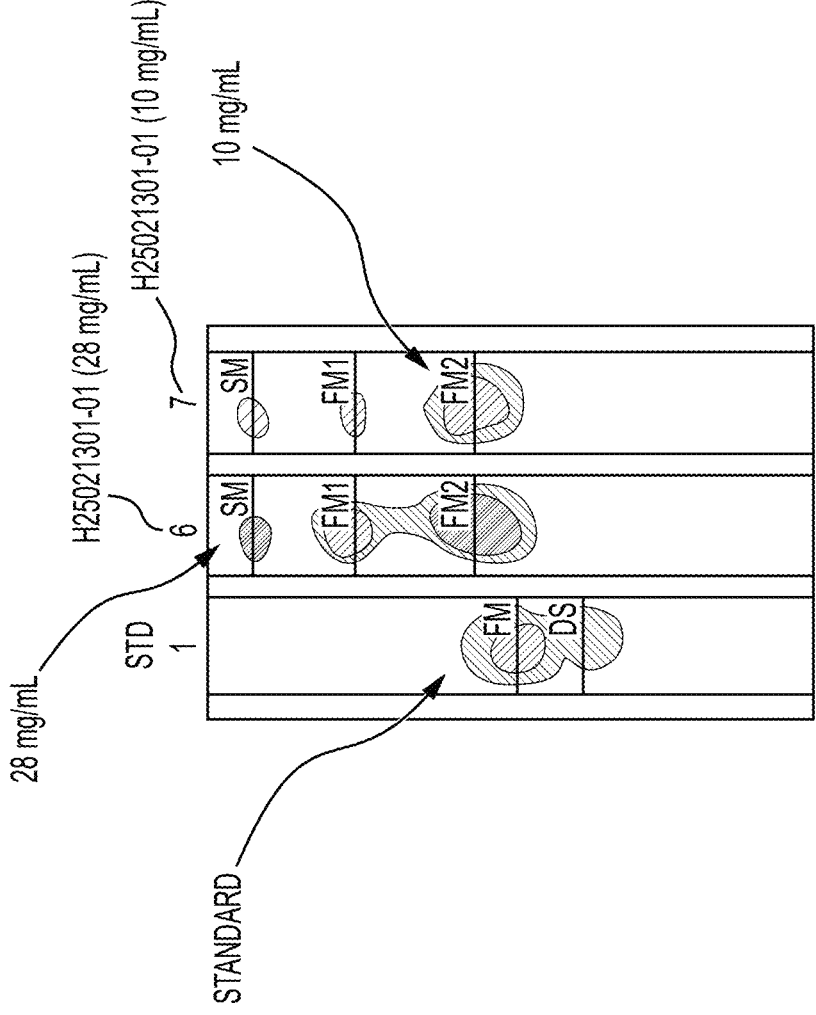
FIG. 3 shows an electrophoresis of sulfodexide sodium and two concentrations of camel heparin sodium.

Referring to FIG. 3, an electrophoresis image of sulodexide sodium and camel heparin sodium is shown. The first column on the left is standard soludexide sodium showing 80% fast moving heparin and 20% dermatan sulfate (DS). The middle column (28 mg/mL) and last column on the right (10 mg/mL) shows the presence of one slow moving part and two fast moving parts, which is characteristic of camel heparin sodium. In this regard, the "fast-moving part" of heparin is a fraction of the overall heparin molecule that is characterized by a lower molecular mass and a lower sulfate group content which results in less charge density compared to the "slow-moving" fraction. This fast-moving component is responsible for a significant portion of heparin's anticoagulant activity, making it crucial for heparin's overall clinical function. The "slow-moving" component in heparin refers to a fraction of the polysaccharide that moves more slowly during agarose-gel electrophoresis, indicating it has a larger molecular size and is more highly sulfated compared to fast-moving heparin fractions. This "slow-moving heparin" is characterized by high anticoagulant activity and is associated with a stronger ability to release lipoprotein lipase (LPL).

Figure 4:
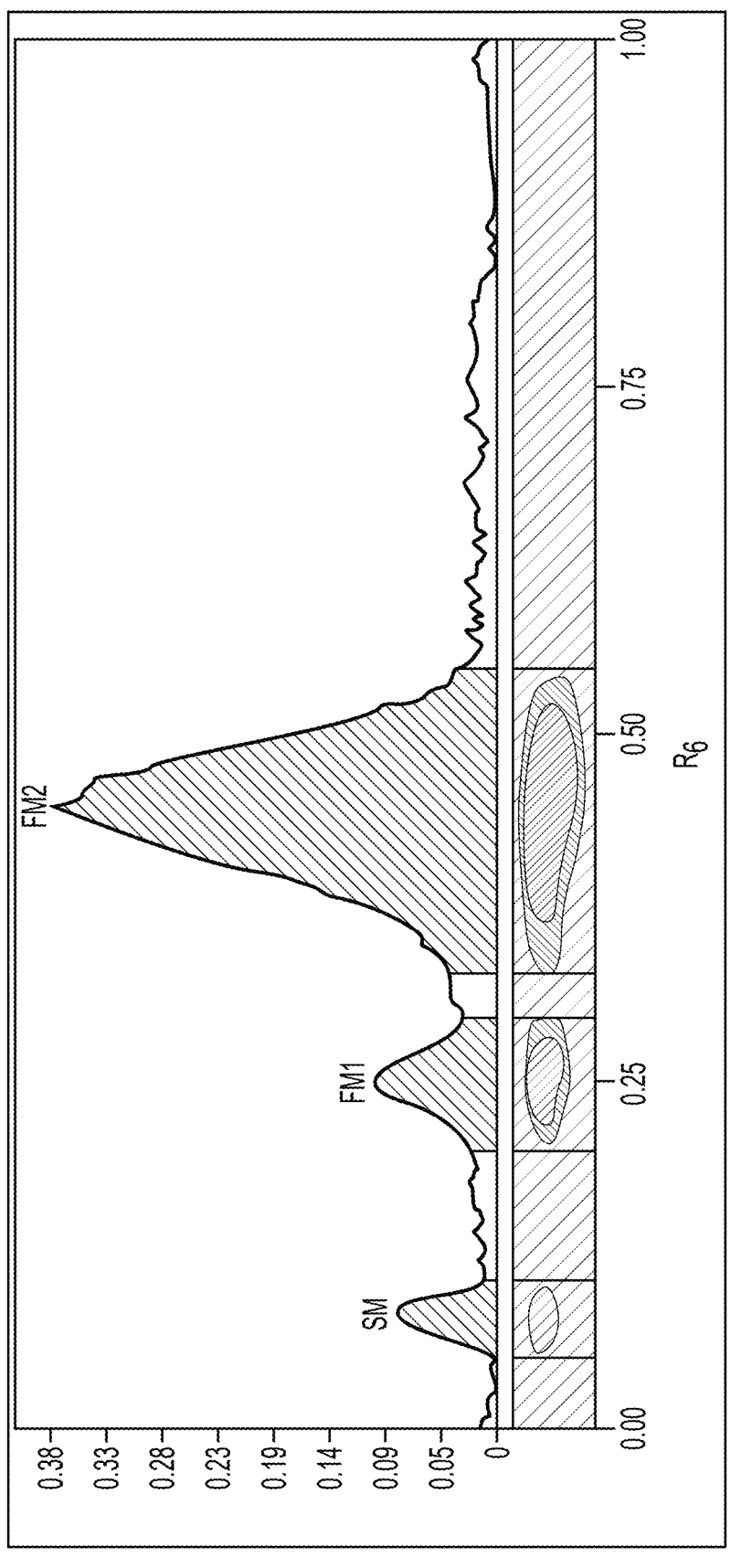
FIG. 4 shows an electrophoresis scanogram of camel heparin sodium at 10 mg/mL concentration.
Figure 5:
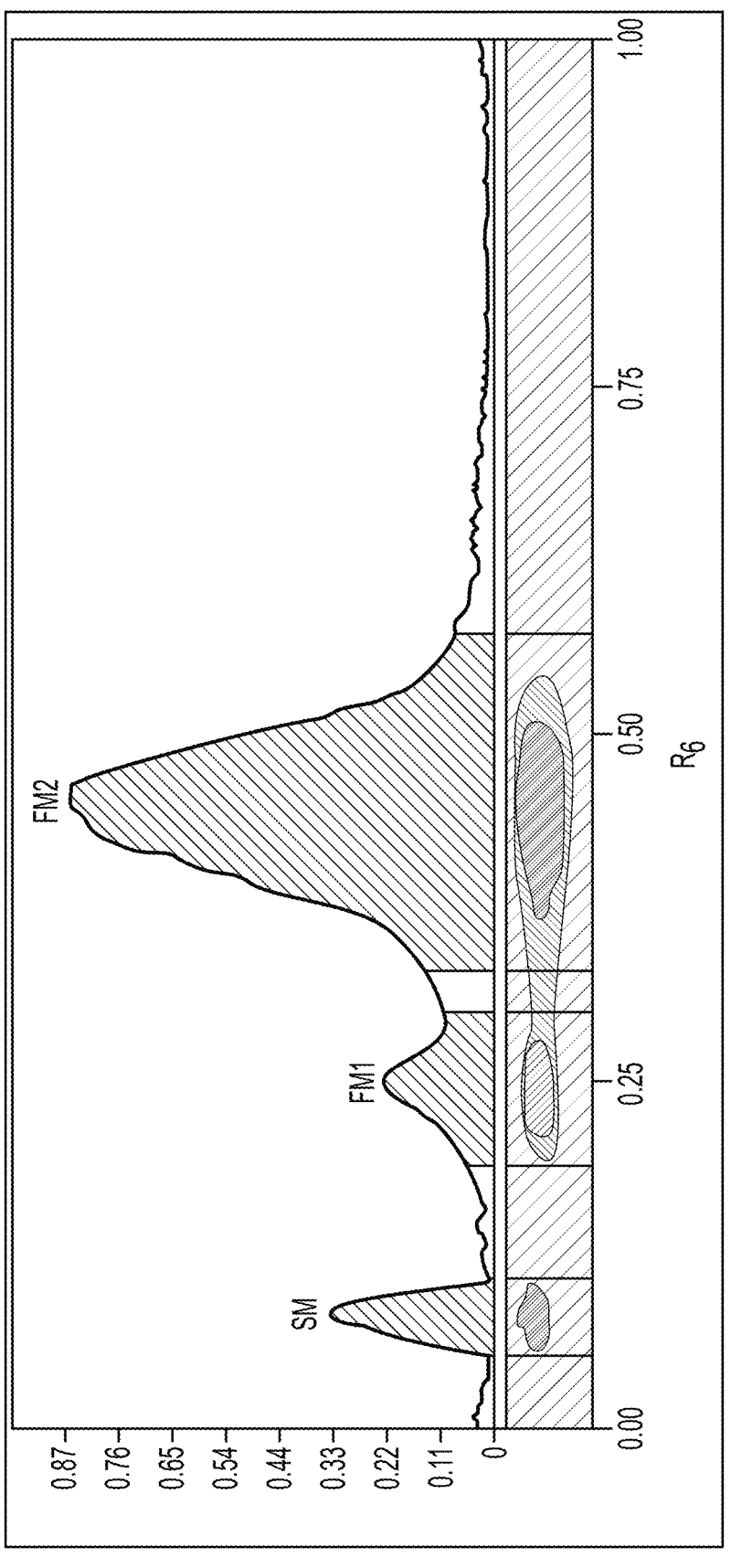
FIG. 5 shows an electrophoresis scanogram of camel heparin sodium at 28 mg/mL concentration.
Figure 6:
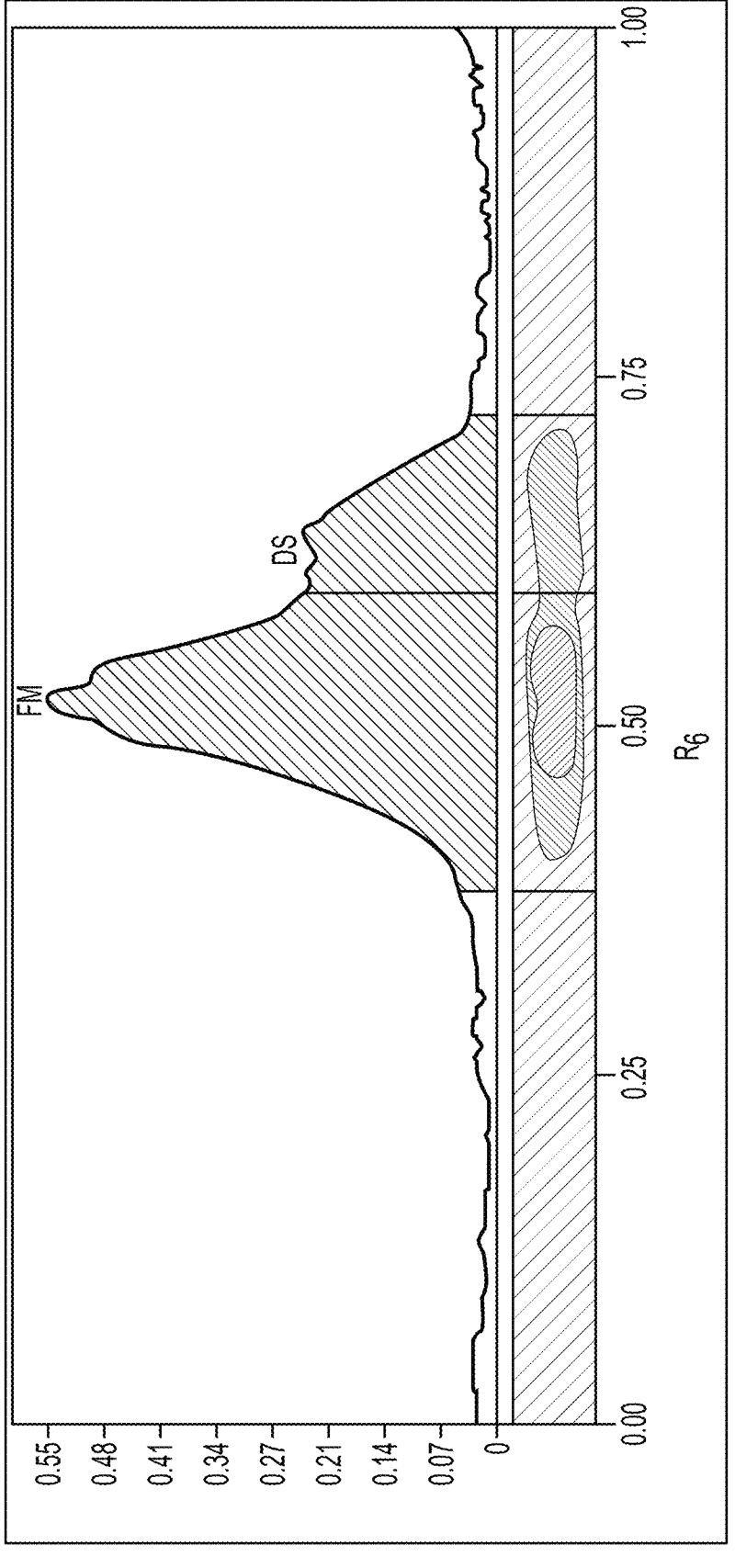
FIG. 6 shows an electrophoresis scanogram of a standard sulodexide sodium.

FIGS. 4, 5, and 6 show the electrophoresis scanograms of camel heparin sodium and sulodexide sodium, respectively. In FIGS. 3 and 4, electrophoresis scanograms show the presence of the two fast moving parts which are special characteristics existing in camel heparin sodium. Heparin from camel intestinal mucosa were extracted and purified, and their structures and physico-chemical properties were evaluated by different techniques. Their structures were determined using disaccharide patterns using specific enzymatic cleavage and relative molecular mass by high-performance size-exclusion chromatography. "Slow moving" and "fast moving" fractions of heparin move in different speeds in agarose gel under proper power supply and therefore were selectively precipitated by barium salt at different places on the gel. The mixtures containing different amounts of these glycosaminoglycans were made and separated by agarose-gel electrophoresis, and these were analyzed quantitatively.

The concentration of camel heparin in FIG. 3 is 10 mg/mL and in FIG. 4 is 28 mg/mL. In FIG. 5, an electrophoresis scanogram shows the typical 80% fast moving heparin (FM) and 20% dermatan sulfate DS of sulodxide sodium.

Figure 7:
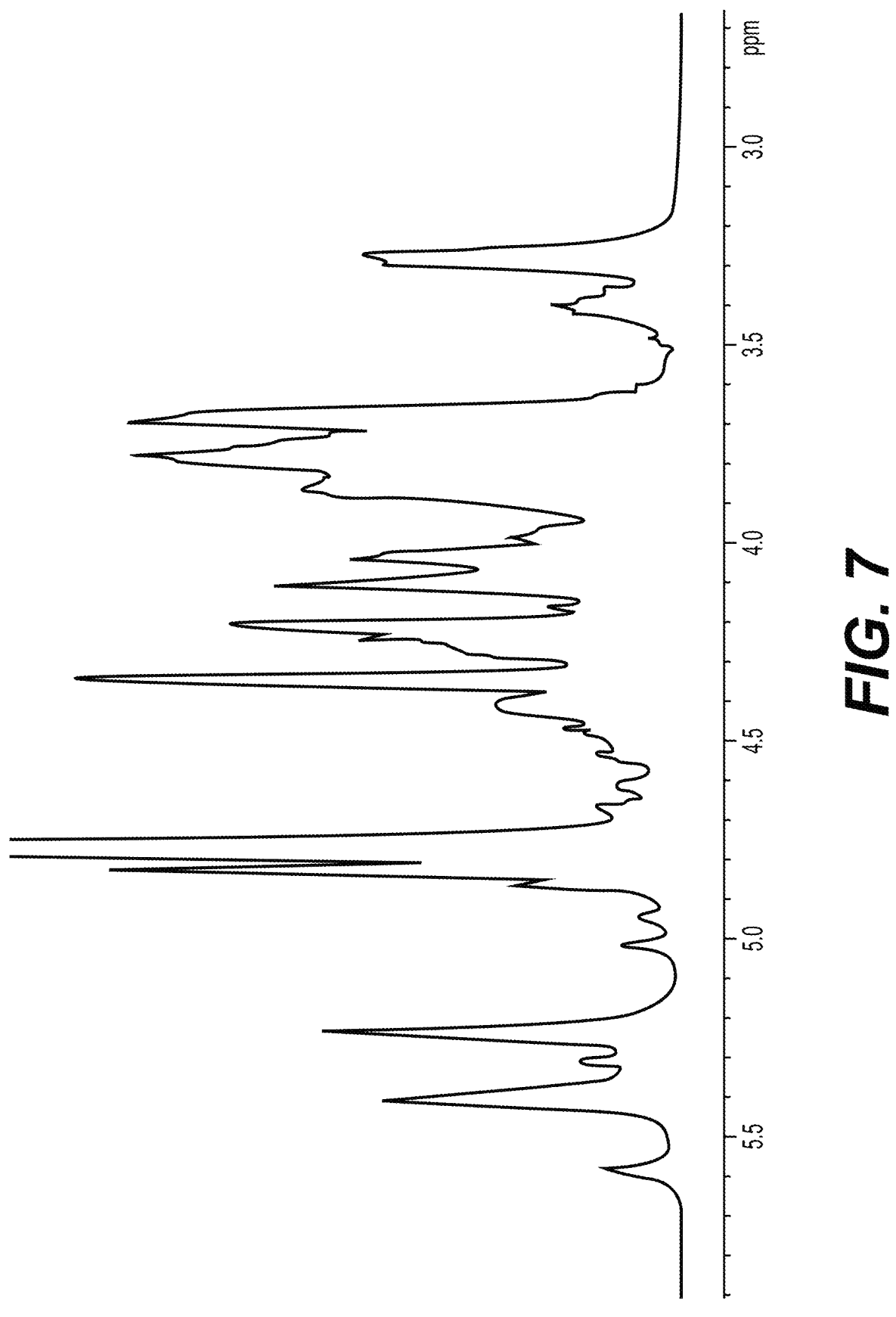
FIG. 7 shows an NMR spectra of camel heparin sodium.
Figure 8:
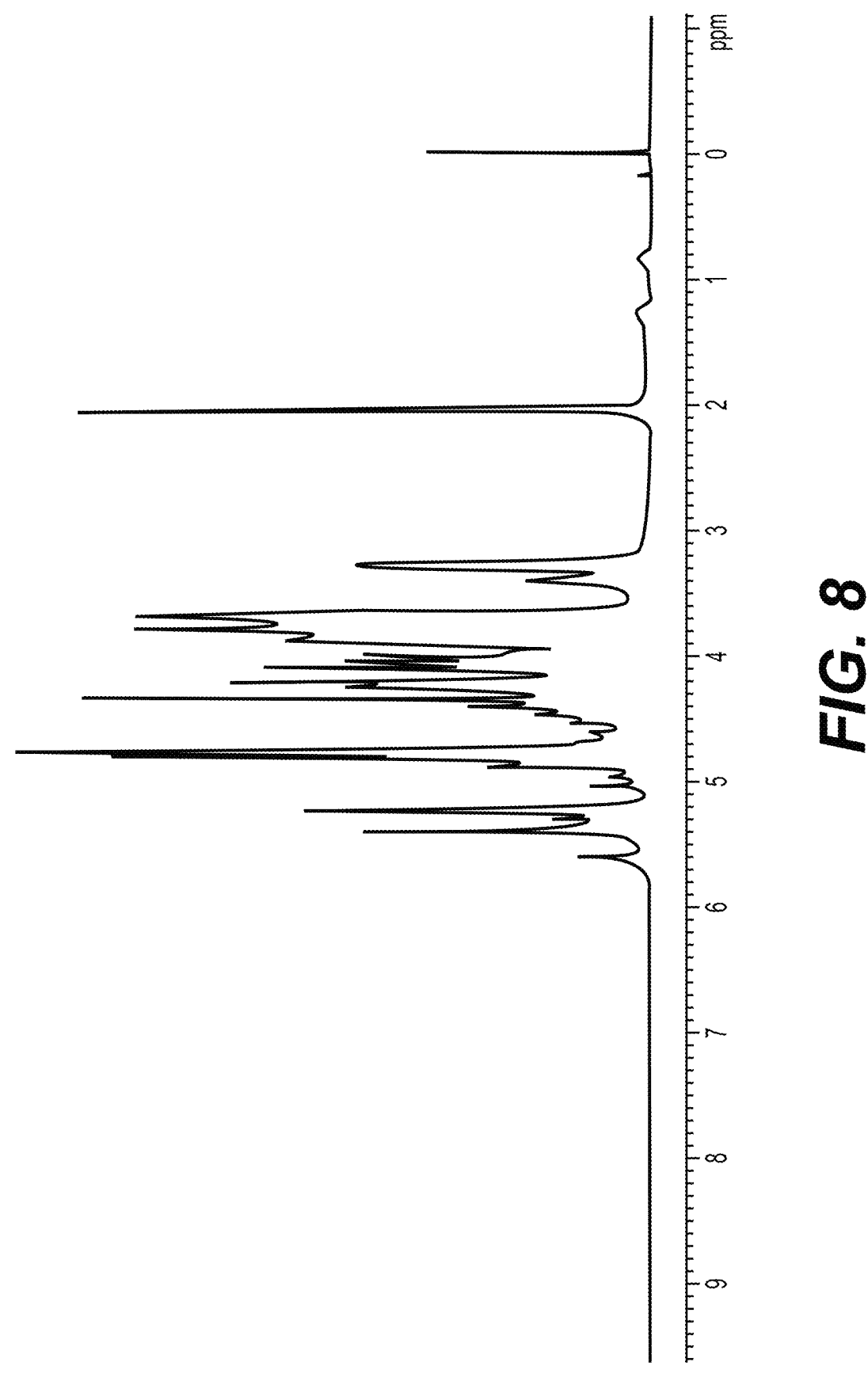
FIG. 8 shows another NMR spectra of camel heparin sodium.
Figure 9:
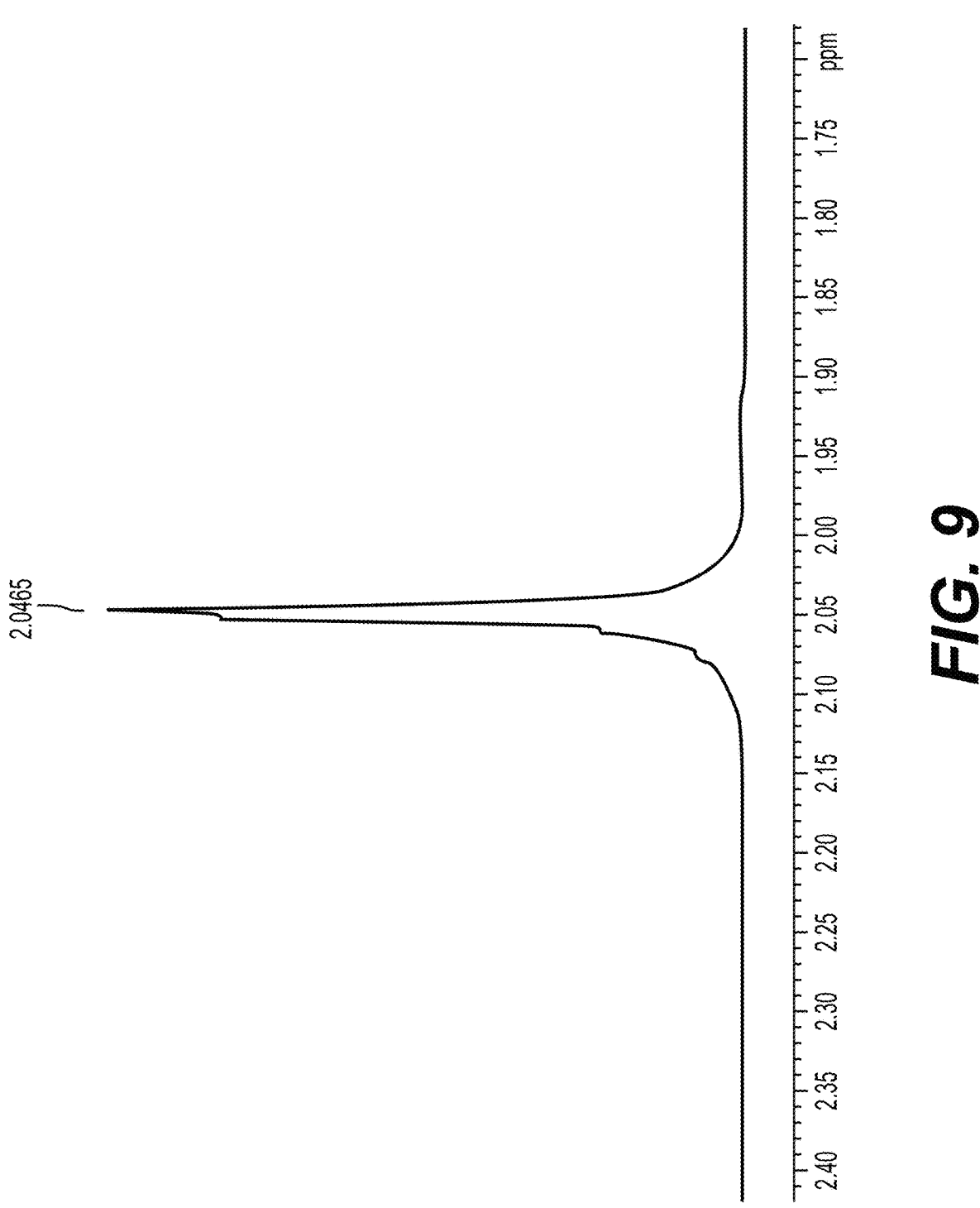
FIG. 9 shows a portion of NMR spectra confirming heparin sodium in camel heparin.

Referring to FIGS. 7, 8, and 9, NMR spectra of camel heparin sodium are illustrated. In FIG. 7, the intensity between 3.35-4.55 ppm has many different variations compared with porcine heparin sodium. FIG. 8, shows heparin sodium signals at 2.04 ppm, 3.27 ppm, 4.34 ppm, 5.22 ppm, and 5.42 ppm. FIG. 9, shows confirmation that the camel heparin sodium has the characteristic molecular structure of heparin sodium at 2.04 ppm.

It is important to note that the intestine needs to be properly massaged as indicated in this disclosure to assure maximum mucosa extracted from mast cells in camel intestines. Important care was applied to extract mucosa after pretreatment at 37.0±1 C° to assure a good quality of mucosa. Proteolysis was carried out together with a calcification process to assure the full removal of organic and inorganic impurities. Proteolysis was combined with nano-filtration to concentrate heparin sodium solution extracted from mucosa of mast cells in the small intestines of camels. A proper organic solvent, iodine free sodium chloride solution, was determined to be needed to precipitate heparin sodium from extracted solution to remove related substances from heparin sodium to assure maximum anticoagulant effectiveness with anti-factor IIa around 120 IU/mg. Anti-factor IIa is a serine protease that is involved in the blood coagulation cascade. Anti-factor IIa activity indicates the ability of heparin to inhibit the enzymatic activity of thrombin. By inhibiting thrombin, anti-factor IIa activity contributes to preventing excessive blood clot formation, thus having an anticoagulant effect.

Further, proper processes, including vaccinating the camels against viral infections, were designed to prevent any potential diseases, including viruses, originated from humped camel transmissible to human beings.

It is to be understood that the method of extracting mucosa from a camel described herein are not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making heparin using mucosa obtained from a camel, the method comprising:

adding calcium chloride to the mucosa to obtain a first mixture, wherein the calcium chloride calcifies the mucosa;

removing excessive calcium chloride from the first mixture by adding sodium carbonate to create a second mixture;

adding bleach to the second mixture to obtain pure mucosa, wherein the bleach comprises about 1% to about 4% w/v $H_2O_2$;

transferring the pure mucosa from the second mixture to a container;

raising the temperature of the pure mucosa;

adding sodium chloride to the pure mucosa to create a third mixture, wherein the sodium chloride is 5-15% w/v and iodine free;

adjusting the pH of the third mixture to a value of about 8 to about 10;

raising the temperature of the third mixture to a temperature ranging from about 40° C. to about 60° C.;

adding protease to the pure mucosa to obtain a fourth mixture and leaving the fourth mixture to react for about 2 hours to about 5 hours;

adding calcium chloride to the fourth mixture to create a fifth mixture, wherein the calcium chloride is a 2-8% solution;

raising the temperature of the fifth mixture to about 80° C. to about 100° C. and leaving the third mixture to react for about 0.5 hours to about 2 hours;

adding sodium carbonate to the fifth mixture to obtain a solution and allowing the solution to react for about 0.5 hours to about 2 hours, wherein the sodium carbonate is a 2-5% solution;

allowing the solution to cool;

centrifuging the cooled solution and collecting a first clear solution;

adjusting a pH of the first clear solution, wherein the pH of the first clear solution is adjusted to a value ranging from about 9 to about 12;

resting the first clear solution for about 0.5 hours to about 2 hours;

centrifuging the first clear solution and collecting a second clear solution;

adjusting a temperature of the second clear solution to about $-10°$ C.;

adjusting the pH of the second clear solution to a value ranging from about 1 to about 4 and resting the second clear solution for about 0.5 hours to about 2 hours;

centrifuging the second clear solution and collecting a third clear solution;

adjusting a pH of the third clear solution to a value ranging from about 9 to about 12;

adding 1-4% w/v $H_2O_2$ to the third clear solution to form a sixth mixture and maintaining the temperature of the sixth mixture at about $20°$ C. to about $30°$ C. for a period of time ranging from about 30 hours to about 50 hours;

centrifuging the sixth mixture and collecting a fourth clear solution;

adjusting a pH of the fourth clear solution to a value ranging from about 9 to about 12, wherein the pH of the fourth clear solution is adjusted by adding 1-3% w/v $H_2O_2$;

maintaining a temperature of the fourth clear solution at a temperature of about $30°$ C. to about $50°$ C. for about 10 hours to about 20 hours;

collecting a fifth clear solution through centrifugation and filtration;

adding a 10-20% w/v iodine free sodium chloride to the fifth clear solution to obtain a seventh mixture;

keeping the seventh mixture overnight;

diluting the seventh mixture with water 5 to 10 times to obtain a sixth mixture;

adding 0.5 volume of pure ethanol into the seventh mixture;

adjusting a temperature of the seventh mixture to about $-30°$ C.;

keeping the seventh mixture overnight; and collecting and drying a pure precipitate to obtain a pure unfractionated heparin (UFH).

2. The method of claim 1, wherein the remaining amount of the pure mucosa is about 40%.

3. The method of claim 1, further comprising filtering the sodium chloride from the mixture to remove proteinic impurity and nucleic impurity, wherein the sodium chloride is filtered out by adjusting the pH of the mixture.

4. The method of claim 1, wherein the fourth clear solution is collected through filtration.

5. The method of claim 1, wherein the seventh mixture is nano-filtered to about 5 to 10% of an original volume of the seventh mixture.

6. The method of claim 1, wherein the pure unfractionated heparin has a molecular weight of about 24,000 Daltons (DA).

7. The method of claim 1, wherein the UFH has a potency of 69.8 IU/mg.

8. The method of claim 1, wherein the UFH has an activated partial thromboplastin (aPPT) of about 69.8 IU/mg.

9. A precipitated heparin sodium produced from the UFH obtained according to the method of claim 1.

10. The precipitated heparin sodium of claim 9, wherein the precipitated heparin sodium has an anti-factor IIa concentration of around 120 IU/mg.

11. A method of removing mucosa from a camel to be used in making the heparin of claim 1, the method comprising:

removing a small intestine of the camel after slaughtering of the camel;

washing the small intestine;

massaging the small intestine;

soaking the small intestine in a water bath;

pressing the small intestine a first time to release about 60% of mucosa from the small intestine;

leaving the small intestine to rest for about 10 minutes; and pressing the small intestine a second time to release a remaining amount of the mucosa in the small intestine.

12. The method of claim 11, wherein water is used for washing the small intestine to remove food residues and impurities inside a wall of the intestine.

13. The method of claim 11, wherein the small intestine is massaged for about 15 minutes.

14. The method of claim 11, wherein a whole portion of the intestine is massaged.

15. The method of claim 11, wherein the water bath is at a temperature of about $37.0°$ C.

16. The method of claim 11, wherein the soaking lasts for about 30 minutes to about 50 minutes.

17. The method of claim 11, wherein pressing the small intestine lasts for about 35 minutes to about 40 minutes.

\* \* \* \* \*